United States Patent
Kessler et al.

(10) Patent No.: US 10,934,252 B1
(45) Date of Patent: Mar. 2, 2021

(54) METHOD FOR PREPARATION OF 2-CHLOROACETOACETIC ACID AMIDE AND ESTER

(71) Applicant: Lonza Solutions AG, Visp (CH)

(72) Inventors: Simon Kessler, Visp (CH); Claudio Arnold, Brig-Glis (CH); Philipp Studer, Visp (CH)

(73) Assignee: Lonza Solutions AG, Visp (CH)

( * ) Notice: Subject to any disclaimer, the term of this patent is extended or adjusted under 35 U.S.C. 154(b) by 0 days.

(21) Appl. No.: 16/978,862

(22) PCT Filed: Mar. 7, 2019

(86) PCT No.: PCT/EP2019/055650
§ 371 (c)(1),
(2) Date: Sep. 8, 2020

(87) PCT Pub. No.: WO2019/170791
PCT Pub. Date: Sep. 12, 2019

Related U.S. Application Data

(60) Provisional application No. 62/640,709, filed on Mar. 9, 2018.

(30) Foreign Application Priority Data

Mar. 9, 2018 (EP) .................................. 18161027
Apr. 24, 2018 (EP) .................................. 18168965

(51) Int. Cl.
*C07C 231/12* (2006.01)
*C07C 231/24* (2006.01)
*C07C 67/317* (2006.01)
*C07C 69/72* (2006.01)
*C07C 235/80* (2006.01)

(52) U.S. Cl.
CPC .......... *C07C 231/12* (2013.01); *C07C 67/317* (2013.01); *C07C 69/72* (2013.01); *C07C 231/24* (2013.01); *C07C 235/80* (2013.01)

(58) Field of Classification Search
None
See application file for complete search history.

(56) References Cited

FOREIGN PATENT DOCUMENTS

| JP | 2017019744 | * | 1/2017 | |
| WO | WO-2019146508 A1 | * | 8/2019 | ........... C07C 231/12 |

OTHER PUBLICATIONS

Gaspa ("Trichloroisocyanuric Acid: a Versatile and Efficient Chlorinating and Oxidizing Reagent" Eur. J. Org. Chem., 2019, p. 3544-3552) (Year: 2019).*
Quinn ("Site-Selective Aliphatic C—H Chlorination Using N-Chloroamides Enables a Synthesis of Chlorolissoclimide" J. Am. Chem. Soc. 2016, 138, p. 696-702) (Year: 2016).*
International Preliminary Report for Patentability and Written Opinion for PCT/EP2019/055650, dated Sep. 15, 2020, 6 pages.
G.F. Mendonca et al., "Trihaloisocyanuric acids as convenient reagents for regioselective halogenation of beta-dicarbonyl compounds", Tetrahedron Letters, vol. 50, No. 4, Nov. 18, 2008, pp. 473-475.
International Search Report for PCT/EP2019/055650, dated Apr. 24, 2019, 2 pages.

* cited by examiner

*Primary Examiner* — Amy C Bonaparte
(74) *Attorney, Agent, or Firm* — Dority & Manning, P.A.

(57) ABSTRACT

The invention discloses a method for the preparation of 2-chloro acetoacetic acid amide or ester by a reaction of acetoacetic acid amide or ester with trichloroisocyanuric acid in the presence of amylene and in the solvent acetone.

15 Claims, No Drawings

METHOD FOR PREPARATION OF 2-CHLOROACETOACETIC ACID AMIDE AND ESTER

CROSS REFERENCE TO RELATED APPLICATIONS

This application is the U.S. National Stage entry of International Application Number PCT/EP2019/055650 filed under the Patent Cooperation Treaty having a filing date of Mar. 7, 2019, which claims priority to European Patent Application No. 18 161 027.0 having a filing date of Mar. 9, 2018, European Patent Application No. 18 168 965.4 having a filing date of Apr. 24, 2018, and U.S. Patent App. No. 62/640,709 having a filing date of Mar. 9, 2018, which are incorporated herein by reference. The invention discloses a method for the preparation of 2-chloro acetoacetic acid amide or ester by a reaction of acetoacetic acid amide or ester with trichloroisocyanuric acid in the presence of amylene and in the solvent acetone.

BACKGROUND OF THE INVENTION

2-Chloro acetoacetic acid amide can be used as bactericidal substance, e.g. as anti fouling agent in aqueous systems.

U.S. Pat. No. 4,214,002 discloses methods and compositions for inhibiting or preventing the growth of microorganisms in aqueous systems wherein the growth is inhibited or prevented by the presence of an effective amount of a 2-chloro-3-oxobutyramide or its derivatives.

JP 2017-019744 A discloses a method for preparation of 2-haloacetoacetic acid amide by halogenating acetoacetic acid amide with a halogenating agent in a solvent. Examples of the solvent include methanol, ethanol, isopropyl alcohol, acetonitrile, propionitrile, N,N-dimethylformamide, N,N-dimethylacetamide, diethyl ether, tetrahydrofuran, methyl t-butyl ether, toluene, xylene, ethylbenzene, monochlorobenzene, o-dichlorobenzene, dichloromethane, 1,2-dichloroethane and water. Selectivities with regard to the di-chlorinated product are between 16% and 28% according to Table 1 in JP 2017-019744 A. Table A is part of Table 1 of JP 2017-019744 A with an additional column showing a ($^A$) Ratio.

($^A$): The Ratio in Table A is the ratio CAAAm:DCAAAm based on their area percentages.

TABLE A

| Solvent | Area Percentage 2-Chloroacetoacetic acid amide | Area Percentage 2,2-Dichloroacetoacetic acid amide | ($^A$) Ratio |
| --- | --- | --- | --- |
| Tetrahydrofuran | 79% | 16% | 4.9 |
| t-Butyl methyl ether | 78% | 14% | 5.6 |
| Monochlorobenzene | 70% | 16% | 4.4 |
| Acetonitrile | 62% | 20% | 3.1 |
| Methanol | 63% | 28% | 2.3 |

The method of instant invention uses acetone as solvent in a reaction of acetoacetic acid amide with trichloroisocyanuric acid, the reaction is done in the presence of amylene. The method improves the selectivity with regard to the monochlorinated versus the di-chlorinated product, the method show good yields and low content of other by products.

In this specification the following abbreviations and substances are used, if not explicitly otherwise stated:
acetoacetic acid amide 3-oxobutanamide, CAS 5977-14-0
acetone CAS 67-64-1 with water content of below 0.2 wt-%
amylene 2-methyl-2-butene, CAS 513-35-9
CAAAm 2-chloro acetoacetic acid amide, 2-chloro-3-oxobutanamide, CAS 67271-66-3
CE Comparative Example
cyanuric acid CAS 108-80-5
DCAAAm 2,2-dichloro acetoacetic acid amide, CAS 22543-23-3
eq. equivalent
Ex Example
TCCA trichloroisocyanuric acid, 1,3,5-trichloro-1,3,5-triazinane-2,4,6-trione), CAS 87-90-1

SUMMARY OF THE INVENTION

Subject of the invention is a method for the preparation of compound of formula (I)

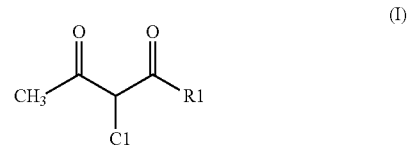

by a reaction REAC1 of compound of formula (II) with trichloroisocyanuric acid;

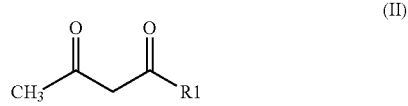

wherein
REAC1 is done in the presence of amylene;
REAC1 is done in the solvent acetone;
R1 is $NH_2$, methoxy or ethoxy.

DETAILED DESCRIPTION OF THE INVENTION

Preferably, R1 is $NH_2$.
Preferably, the molar amount of trichloroisocyanuric acid in REAC1 is from 0.35 to 0.75 times, more preferably from 0.36 to 0.7 times, even more preferably from 0.37 to 0.6 times, especially from 0.38 to 0.55 times, more especially from 0.40 to 0.47 times, of the molar amount of compound of formula (II).
Preferably, the molar amount of amylene in REAC1 is from 0.05 to 0.12 times, more preferably from 0.06 to 0.11 times, even more preferably from 0.07 to 0.11 times, of the molar amount of compound of formula (II);
these molar amounts of amylene acid in REAC1 are also called "total amount of amylene in REAC1" or "total amounts of amylene in REAC1" in this specification.
Preferably, in REAC1 the trichloroisocyanuric acid is charged to the compound of formula (II).
In a preferred embodiment, one part of the amylene is used for REAC1 in form of a mixture of amylene with trichloroisocyanuric acid, and the remaining part of the amylene is used for REAC1 in form of a mixture of amylene with compound of formula (II);

preferably, the molar amount of amylene acid in the mixture of amylene with trichloroisocyanuric acid is from 0.08 to 0.2 times, more preferably from 0.09 to 0.175 times, even more preferably from 0.09 to 0.16 times, of the molar amount of trichloroisocyanuric acid; and the molar amount of amylene acid in the mixture of amylene with compound of formula (II) is from 0.01 to 0.1 times, more preferably from 0.015 to 0.07 times, even more preferably from 0.02 to 0.07 times, of the molar amount of compound of formula (II);

with the amounts of these two parts of amylene adding up to the total amounts of amylene in REAC1.

More preferably, one half of the total amount of amylene in REAC1 is used in form of the mixture of amylene with trichloroisocyanuric acid, and the other half of the total amount of amylene in REAC1 is used in form of the mixture of amylene with compound of formula (II).

More preferably, in REAC1 the mixture of amylene with trichloroisocyanuric acid is charged to the mixture of amylene with compound of formula (II).

Preferably, the mixture of amylene with trichlorocyanuric acid is prepared by charging the amylene to the trichlorocyanurid acid;

Preferably, the weight of acetone in REAC1 is from 2.5 to 100 times, more preferably from 4 to 50 times, even more preferably from 5 to 30 times, especially from 5 to 20 times, more especially from 6 to 15 times, of the weight of compound of formula (II);

this weight of acetone in REAC1 is also called "total weight of acetone in REAC1" or "total weights of acetone in REAC1" in this specification.

Preferably, said mixture of amylene with trichloroisocyanuric acid is used in form of a solution in acetone; and said mixture of amylene with compound of formula (II) is in form of a solution in acetone.

More preferably, the weight of the acetone in said solution in acetone of the mixture of amylene with trichloroisocyanuric acid is from 2 to 9 times, more preferably from 2.2 to 8 times, even more preferably from 2.3 to 6 times, especially from 2.4 to 5 times, of the weight of trichloroisocyanuric acid;

and the weight of the acetone in said solution in acetone of the mixture of amylene with compound of formula (II) is from 2 to 9 times, more preferably from 2.5 to 8 times, even more preferably from 5 to 7 times, especially from 3 to 7 times, more especially from 3.5 to 7 times, of the weight of compound of formula (II);

with the weight of the acetone in said solution of the mixture of amylene with trichloroisocyanuric acid and the weight of acetone in said solution of the mixture of amylene with compound of formula (II) adding up to the total weight of acetone in REAC1.

Preferably, the trichloroisocyanuric acid is used for the preparation of said mixture of amylene with trichloroisocyanuric acid in form of a solution of trichloroisocyanuric acid in acetone.

Preferably, the part of the amylene, that is used for the preparation of the mixture of amylene with trichloroisocyanuric acid, is used for the preparation of said mixture in form of a solution of amylene in acetone.

More preferably, the weight of the acetone in said solution of trichloroisocyanuric acid in acetone is from 1.5 to 4 times, more preferably from 1.6 to 3.7 times, even more preferably from 1.7 to 3.4 times, especially from 1.8 to 3.1 times, of the weight of trichloroisocyanuric acid;

and the weight of the acetone in said solution of amylene in acetone is of from 10 to 40 times, more preferably from 11 to 38 times, even more preferably from 12 to 37 times, especially from 13 to 37 times, more especially from 14 to 37 times, of the weight of amylene;

with the weight of the acetone in said solution of trichloroisocyanuric acid in acetone and the weight of the acetone in said solution of amylene in acetone adding up to the stated weight of the acetone in said solution in acetone of the mixture of amylene with trichloroisocyanuric acid.

More preferably, the solution in acetone of the mixture of amylene with trichlorocyanuric acid is prepared by charging the solution of amylene in acetone to the solution of trichlorocyanuric acid in acetone.

Preferably, the charging time for charging the amylene to the trichlorocyanuric acid is from 0.1 to 5 h, more preferably from 0.2 to 4 h, even more preferably from 0.3 to 3 h.

Preferably, the temperature during the charging of the amylene to the trichlorocyanuric acid is from −10 to 30° C., more preferably from −5 to 25° C., even more preferably from −2 to 22° C.

Preferably, the reaction temperature of REAC1 is from −10 to 30° C., more preferably from −5 to 25° C., even more preferably from −2 to 22° C.

Preferably, the reaction time of REAC1 is from 0.5 to 24 h, more preferably from 0.5 to 24 h, even more preferably from 2 to 24 h, especially from 2 to 24 h.

When in REAC1 the trichloroisocyanuric acid is charged to the compound of formula (II), then the time for charging of the trichloroisocyanuric acid to the compound of formula (II) is preferably from 0.5 to 12 h, more preferably from 1 to 10 h;

this time for charging is part of the reaction time.

Preferably, REAC1 is done under atmospheric pressure or under elevated pressure, such as from atmospheric pressure to 100 bar, more preferably, REAC1 is done under atmospheric pressure.

Elevated pressure can be applied by used of an inert gas such as argon.

In REAC1 cyanuric acid is formed as a by product. REAC1 provides a reaction mixture, from which compound of formula (I) can be isolated; the solvent of said reaction mixture is acetone.

After REAC1, compound of formula (I) can be isolated from the reaction mixture, that is provided by REAC1, by standard methods such as evaporation of volatile components, removal of solid substances from the reaction mixture by filtration, distillation, preferably under reduced pressure, extraction, washing, drying, concentration, crystallization, preferably crystallization by an exchange of acetone against another solvent, which is better suited for crystallization, such as dichloroethane, and subsequent crystallization, chromatography or a combination thereof, which are known per se to the person skilled in the art.

Preferably, after REAC1 any cyanuric acid, which is formed in REAC1 as by product, is separated from the reaction mixture, preferably by filtration, this filtration provides a filtrate.

Then preferably the acetone in the filtrate is completely or partly removed by distillation providing a residue fraction either without or with residual acetone.

During the removal of acetone from the reaction mixture by distillation the removed acetone can be substituted by dichloroethane.

Preferably in case of a residue fraction with residual acetone is obtained from the distillation, the distillation of the residue fraction is continued while exchanging the remaining acetone against dichloroethane. Then preferably after said exchange of acetone against dichloroethane the desired compound of formula (I) is isolated by crystallization.

More preferably, the cyanuric acid, that is formed in REAC1 as a by-product, is separated from the reaction mixture after REAC1, preferably by filtration.

More preferably, the solvent acetone of the reaction mixture is exchanged after REAC1 against dichloroethane, preferably during a distillation.

Even more preferably, said exchange of acetone against dichloroethane is done during a distillation which removes acetone while dichloroethane is added.

Especially, said exchange of acetone against dichloroethane is done after said separation of cyanuric acid from the reaction mixture.

Preferably, compound of formula (I) is isolated by crystallization from dichloroethane.

So in one embodiment of the invention, after REAC1 cyanuric acid, that is formed in REAC1 as a by-product, is separated from the reaction mixture after REAC1, preferably by filtration; then the solvent acetone of the reaction mixture is exchanged against dichloroethane, preferably during a distillation; preferably during a distillation which removes the solvent acetone while dichloroethane is added, and then compound of formula (I) is isolated by crystallization from said dichloroethane.

EXAMPLES

Methods

Purity, content and yield of acetoacetic acid amide, CAAAm, DCAAAm and of cyanuric acid in the product were determined by $^1$H-NMR.

Examples 1 to 5 & Comparative Example 1
(Optimization Amylene Stabilization)

TABLE 1

Optimization of reaction conditions with amylene-additive.

| Entry | eq. TCCA | T [° C.] | t [h] | eq. amylene precharged/in TCCA | ($^1$) Yield CAAAm | ($^2$) Ratio |
|---|---|---|---|---|---|---|
| CEx 1 | 0.41 | 20 | 2 | —/— | 10.9% | 0.2 |
| Ex 1 | 0.41 | 20 | 8 | 0.05/0.05 | 61.3% | 15.9 |
| Ex 2 | 0.41 | 20 | 5 | 0.05/0.05 | 70.9% | 10.5 |
| Ex 3 | 0.41 | 10 | 5 | 0.05/0.05 | 77.0% | 18.8 |
| Ex 4 | 0.41 | 0 | 5 | 0.05/0.05 | 77.7% | 17.2 |
| Ex 5 | 0.43 | 10 | 5 | 0.05/0.05 | 79.3% | 17.7 |

($^1$) Yield: Yield of CAAAm based on substrate acetoacetic acid amide in the filtrate after removal of cyanuric acid.
($^2$) Ratio: Molar ratio CAAAm:DCAAAm based on the NMR area of respective signal in the filtrate after removal of cyanuric acid.
The eq. are molar equivalents in respect of acetoacetic acid amide Procedure for the Entries in Table 1:

TCCA (x eq) was dissolved in 55 g acetone. In examples 1 to 5, a solution of amylene (x eq, denoted in Table 1 with "eq. amylene in TCCA") in 25 g acetone was then added within 30 min at the same temperature T, providing a trichloroisocyanuric acid-amylene solution. In CEx1 this TCCA solution in acetone, in examples 1 to 5 this trichloroisocyanuric acid-amylene solution, was added at the temperature T and during the charging time t to a solution of 20 g of acetoacetic acid amide (198 mmol, 1 eq) and amylene (x eq, denoted in Table 1 with "eq. amylene precharged") in 120 g acetone. The reaction mixture was stirred for 1 h at the temperature T, then the reaction mixture was allowed to warm to room temperature and was then cooled to 0° C. The precipitated cyanuric acid was filtered off and the yield in the filtrate was analyzed via $^1$H-NMR, values are given in Table 1.

Example 6

42.2 g of trichloroisocyanuric acid (0.46 eq) were dissolved in 110 g acetone. At 0° C. a solution of 1.4 g amylene (0.05 eq) in 50 g acetone was added within 30 min providing a trichloroisocyanuric acid-amylene solution. This trichloroisocyanuric acid-amylene solution was added at 0° C. within 6 h to a solution of acetoacetic acid amide (40 g, 1 eq) and 1.4 g of amylene (0.05 eq) in 240 g acetone. The reaction mixture was stirred for 3 h at 0° C., then the reaction mixture was allowed to warm to room temperature, and was then stirred for 30 min at room temperature and cooled to 0° C. within 30 min.

The precipitated cyanuric acid was filtered off providing a filtrate. Then ca. 270 g of the acetone in the filtrate was removed by distillation providing a residue fraction. The distillation of the residue fraction was continued while exchanging the remaining acetone with dichloroethane by adding a total amount of 400 g of dichloroethane over 1.5 h whilst continuously distilling off 370 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 76.3%

Ratio: Molar ratio CAAAm:DCAAAm based on the NMR area of respective signal in the filtrate after removal of cyanuric acid: 6.7

Isolated yield was 63.4% of 2-chloro acetoacetic acid amide in the product with respect to the substrate acetoacetic acid amide.

Purity of the 2-chloro acetoacetic acid amide was 97.4 wt-%.

Content of acetoacetic acid amide in the product was 0.2 wt-%.

Content of 2,2-dichloro acetoacetic acid amide in the product was 0.7 wt-%.

Content of cyanuric acid in the product was 1.7 wt-%.

Example 7

77.6 g of trichloroisocyanuric acid (0.43 eq) were dissolved in 220 g acetone. At 10° C. a solution of 2.8 g amylene (0.05 eq) in 100 g acetone was added within 2 h providing a trichloroisocyanuric acid-amylene solution. This trichloroisocyanuric acid-amylene solution was added at 10° C. within 3 h to a solution of 80 g of acetoacetic acid amide (1 eq) and 2.8 g of amylene (0.05 eq) in 480 g acetone. The reaction mixture was cooled to 0° C. and the precipitated cyanuric acid was filtered off providing a filtrate. Then ca. 585 g of the acetone in the filtrate was removed by distillation providing a residue fraction. The distillation of the residue fraction was continued while exchanging the remaining acetone with dichloroethane by adding a total amount of 118 g of dichloroethane over 1 h whilst continuously distilling off 68 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 80.5%

Ratio: Molar ratio CAAAm:DCAAAm based on the NMR area of respective signal in the filtrate after removal of cyanuric acid: 16.1

Isolated yield was 69.7% of 2-chloro acetoacetic acid amide in the product with respect to the substrate acetoacetic acid amide.

Purity of the 2-chloro acetoacetic acid amide was 96.4 wt-%.

Content of acetoacetic acid amide in the product was 0.8 wt-%.

Content of 2,2-dichloro acetoacetic acid amide in the product was 0.9 wt-%.

Content of cyanuric acid in the product was 1.9 wt-%.

Example 8

80.9 g of trichloroisocyanuric acid (0.44 eq) were dissolved in 220 g acetone. At 10° C. a solution of 2.8 g amylene (0.05 eq) in 100 g acetone was added within 2 h providing a trichloroisocyanuric acid-amylene solution. This trichloroisocyanuric acid-amylene solution was added at 10° C. within 5 h to a solution of 80 g of acetoacetic acid amide (1 eq) and 2.8 g of amylene (0.05 eq) in 480 g acetone. The reaction mixture was cooled to 0° C. and the precipitated cyanuric acid was filtered off providing a filtrate. Then ca. 606 g of the acetone in the filtrate was removed by distillation providing a residue fraction. The distillation of the residue fraction was continued while exchanging the remaining acetone with dichloroethane by adding a total amount of 102 g of dichloroethane over 1 h whilst continuously distilling off 52 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 76.3%

Ratio: Molar ratio CAAAm:DCAAAm based on the NMR area of respective signal in the filtrate after removal of cyanuric acid: 11.4

Isolated yield was 67.1% of 2-chloro acetoacetic acid amide in the product with respect to the substrate acetoacetic acid amide.

Purity of the 2-chloro acetoacetic acid amide was 97.7 wt-%.

Content of acetoacetic acid amide in the product was 0.1 wt-%.

Content of 2,2-dichloro acetoacetic acid amide in the product was 0.5 wt-%.

Content of cyanuric acid in the product was 1.7 wt-%.

Example 9

94.4 g of trichloroisocyanuric acid (0.51 eq) were dissolved in 180 g acetone. At 10° C. a solution of 4.12 g amylene (0.075 eq) in 60 g acetone was added within 2 h providing a trichloroisocyanuric acid-amylene solution. This trichloroisocyanuric acid-amylene solution was added at 10° C. within 1.9 h to a solution of 80 g of acetoacetic acid amide (1 eq) and 1.37 g of amylene (0.025 eq) in 293 g acetone. The reaction mixture was cooled to 0° C. and the precipitated cyanuric acid was filtered off providing a filtrate. Then 420 g of the acetone in the filtrate was removed by distillation providing a residue fraction. The distillation of the residue fraction was continued while exchanging the remaining acetone with dichloroethane by adding a total amount of 165 g of dichloroethane over 1.5 h whilst continuously distilling off 91 g of a mixture of acetone and dichloroethane.

After this distillation, the desired product 2-chloro acetoacetic acid amide was isolated by crystallization via cooling of the residue fraction to 0° C.

Yield: Yield of CAAAm based on substrate acetoacetic acid amide in the filtrate after removal of cyanuric acid: 75.3%.

Ratio: Molar ratio CAAAm:DCAAAm based on the NMR area of respective signal in the filtrate after removal of cyanuric acid: 7.2

Isolated yield was 64.4% of 2-chloro acetoacetic acid amide in the product with respect to the substrate acetoacetic acid amide.

Purity of the 2-chloro acetoacetic acid amide was 97.4 wt-%.

Content of acetoacetic acid amide in the product was 0.1 wt-%.

Content of 2,2-dichloro acetoacetic acid amide in the product was 0.7 wt-%.

Content of cyanuric acid in the product was 1.8 wt-%.

Example 10

91.03 g of trichloroisocyanuric acid (0.50 eq) were dissolved in 180 g acetone. At 10° C. a solution of 4.21 g amylene (0.075 eq) in 60 g acetone was added within 2 h providing a trichloroisocyanuric acid-amylene solution. This trichloroisocyanuric acid-amylene solution was added at 10° C. within 2.65 h to a solution of 80 g of acetoacetic acid amide (1 eq) and 1.37 g of amylene (0.025 eq) in 293 g acetone. The reaction mixture was cooled to 0° C. and the precipitated cyanuric acid was filtered off providing a filtrate. Then 425 g of the acetone in the filtrate was removed by distillation providing a residue fraction. The distillation of the residue fraction was continued while exchanging the remaining acetone with dichloroethane by adding a total amount of 81 g of dichloroethane over 1 h whilst continuously distilling off 58 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 70.3%.

Ratio: Molar ratio CAAAm:DCAAAm based on the NMR area of respective signal in the filtrate after removal of cyanuric acid: 7.8

Isolated yield was 56.8% of 2-chloro acetoacetic acid amide in the product with respect to the substrate acetoacetic acid amide.

Purity of the 2-chloro acetoacetic acid amide was 97.0 wt-%.

Content of acetoacetic acid amide in the product was 0.4 wt-%.

Content of 2,2-dichloro acetoacetic acid amide in the product was 0.8 wt-%.

Content of cyanuric acid in the product was 1.8 wt-%.

Example 11

87.7 g of trichloroisocyanuric acid (0.48 eq) were dissolved in 180 g acetone. At 10° C. a solution of 4.12 g amylene (0.075 eq) in 60 g acetone was added within 2 h providing a trichloroisocyanuric acid-amylene solution. This trichloroisocyanuric acid-amylene solution was added at 10° C. within 2.7 h to a solution of 80 g of acetoacetic acid amide (1 eq) and 1.37 g of amylene (0.025 eq) in 293 g acetone. The reaction mixture was cooled to 0° C. and the precipitated cyanuric acid was filtered off providing a filtrate. Then 448 g of the acetone in the filtrate was removed by distillation providing a residue fraction. The distillation of the residue fraction was continued while exchanging the remaining acetone with dichloroethane by adding a total amount of 93 g of dichloroethane over 0.8 h whilst continuously distilling off 72 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 74.5%.

Ratio: Molar ratio CAAAm:DCAAAm based on the NMR area of respective signal in the filtrate after removal of cyanuric acid: 15.6

Isolated yield was 54.5% of 2-chloro acetoacetic acid amide in the product with respect to the substrate acetoacetic acid amide.

Purity of the 2-chloro acetoacetic acid amide was 98.1 wt-%.

Content of acetoacetic acid amide in the product was 0.5 wt-%.

Content of 2,2-dichloro acetoacetic acid amide in the product was 0.2 wt-%.

Content of cyanuric acid in the product was 1.2 wt-%.

Example 12

77.55 g of trichloroisocyanuric acid (0.43 eq) were dissolved in 220 g acetone. At 10° C. a solution of 2.75 g amylene (0.05 eq) in 100 g acetone was added within 2 h providing a trichloroisocyanuric acid-amylene solution. This trichloroisocyanuric acid-amylene solution was added at 10° C. within 3.4 h to a solution of 80 g of acetoacetic acid amide (1 eq) and 1.37 g of amylene (0.05 eq) in 480 g acetone. The reaction mixture was cooled to 0° C. and the precipitated cyanuric acid was filtered off providing a filtrate. Then 719 g of the acetone in the filtrate was removed by distillation providing a residue fraction. The distillation of the residue fraction was continued while exchanging the remaining acetone with dichloroethane by adding a total amount of 145 g of dichloroethane over 25 min whilst continuously distilling off 79 g of a mixture of acetone and dichloroethane.

After this distillation, the desired product 2-chloro acetoacetic acid amide was isolated by crystallization via cooling of the residue fraction within 2 h to 0° C.

Yield: Yield of CAAAm based on substrate acetoacetic acid amide in the filtrate after removal of cyanuric acid: 79.8%.

Ratio: Molar ratio CAAAm:DCAAAm based on the NMR area of respective signal in the filtrate after removal of cyanuric acid: 18.8

Isolated yield was 67.9% of 2-chloro acetoacetic acid amide in the product with respect to the substrate acetoacetic acid amide.

Purity of the 2-chloro acetoacetic acid amide was 97.7 wt-%.

Content of acetoacetic acid amide in the product was 0.1 wt-%.

Content of 2,2-dichloro acetoacetic acid amide in the product was 0.1 wt-%.

Content of cyanuric acid in the product was 2.0 wt-%.

The invention claimed is:

1. A method for the preparation of a compound of formula (I)

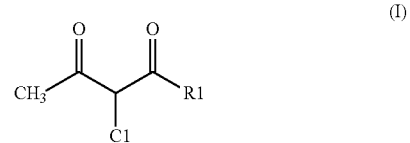

by a reaction REAC1 of a compound of formula (II) with trichloroisocyanuric acid;

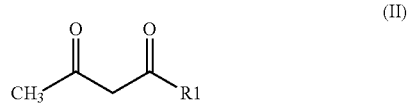

wherein
REAC1 is done in the presence of amylene;
REAC1 is done in the solvent acetone;
R1 is $NH_2$, methoxy or ethoxy.

2. The method according to claim 1, wherein
R1 is $NH_2$.

3. The method according to claim 1, wherein
in REAC1 the trichloroisocyanuric acid is charged to the compound of formula (II).

4. The method according to claim 1, wherein one portion of the amylene is used for REAC1 in form of a mixture of amylene with trichloroisocyanuric acid, and the remaining portion of the amylene is used for REAC1 in form of a mixture of amylene with the compound of formula (II).

5. The method according to claim 4, wherein
in REAC1 the mixture of amylene with trichloroisocyanuric acid is charged to the mixture of amylene with the compound of formula (II).

6. The method according to claim 4, wherein
the mixture of amylene with trichloroisocyanuric acid is prepared by charging the amylene to the trichloroisocyanuric acid.

7. The method according to claim 4, wherein the mixture of amylene with trichloroisocyanuric acid is used in form of a solution in acetone; and the mixture of amylene with compound of formula (II) is in form of a solution in acetone.

8. The method according to claim 7, wherein
the trichloroisocyanuric acid is used for the preparation of the mixture of amylene with trichloroisocyanuric acid in the form of a solution of trichloroisocyanuric acid in acetone.

9. The method according to claim 7, wherein
the part of the amylene, that is used for the preparation of the mixture of amylene with trichloroisocyanuric acid, is used for the preparation of the mixture in form of a solution of amylene in acetone.

10. The method according to claim 7, wherein
the solution in acetone of the mixture of amylene with trichlorocyanuric acid is prepared by charging a solution of amylene in acetone to a solution of trichloroisocyanuric acid in acetone.

11. The method according to claim 1, wherein cyanuric acid, that is formed in REAC1 as a by product, is separated from the reaction mixture after REAC1.

12. The method according to claim 11, wherein
cyanuric acid, that is formed in REAC1 as a by-product, is separated from the reaction mixture after REAC1 by filtration.

13. The method according to claim 11, wherein the solvent acetone of the reaction mixture is exchanged after REAC1 with dichloroethane.

14. The method according to claim 13, wherein
the exchange of acetone with dichloroethane is done after the separation of cyanuric acid from the reaction mixture.

15. The method according to claim 13, wherein the compound of formula (I) is isolated by crystallization from dichloroethane.

* * * * *